United States Patent [19]
Goble et al.

[11] Patent Number: 5,417,692
[45] Date of Patent: May 23, 1995

[54] BONE FIXATION AND FUSION SYSTEM

[76] Inventors: E. Marlowe Goble, 850 E. 1200 North, Logan, Utah 84321; Gregory S. Anderson, #4 Ravenwood, Sandy, Utah 84092; David P. Luman, 1430 E. 1260 North, Logan, Utah 84321

[21] Appl. No.: 177,752

[22] Filed: Jan. 4, 1994

[51] Int. Cl.$^6$ ............................................. A61B 17/58
[52] U.S. Cl. ........................................ 606/73; 606/104; 433/173; 433/174
[58] Field of Search .................. 606/53, 60, 62, 65, 606/72, 73, 75, 104; 623/21; 433/74, 191, 193–195, 201.1, 173, 174, 175, 176; 411/383, 389; 403/280, 282, 313, 361

[56] References Cited

U.S. PATENT DOCUMENTS

| | | | |
|---|---|---|---|
| 64,654 | 5/1867 | Floyd | 403/361 |
| 184,718 | 11/1876 | Lewis | 403/280 |
| 1,897,196 | 2/1933 | Hunt | 411/389 |
| 2,570,465 | 10/1951 | Lundholm . | |
| 3,103,926 | 9/1963 | Cochran et al. . | |
| 3,744,488 | 7/1973 | Cox . | |
| 4,278,091 | 7/1981 | Borzone . | |
| 4,388,921 | 6/1983 | Sutter et al. . | |
| 4,409,974 | 10/1983 | Freedland . | |
| 4,414,967 | 11/1983 | Shapiro . | |
| 4,438,769 | 3/1984 | Pratt et al. . | |
| 4,463,753 | 8/1984 | Gustilo | 606/73 |
| 4,570,624 | 2/1986 | Wu . | |
| 4,607,638 | 8/1986 | Crainich . | |
| 4,688,561 | 8/1987 | Reese . | |
| 4,723,540 | 2/1988 | Gilmer, Jr. . | |
| 4,838,254 | 6/1989 | Gauthier . | |
| 4,913,144 | 4/1990 | Del Medico | 606/75 |
| 4,927,421 | 5/1990 | Goble et al. | 606/73 |
| 5,037,426 | 8/1991 | Goble et al. | 606/96 |
| 5,053,038 | 10/1991 | Sheehan | 606/75 |
| 5,167,665 | 12/1992 | McKinney . | |

OTHER PUBLICATIONS

Zimmer Brochure Catalog, 5 pages, 1987.

*Primary Examiner*—Tamara L. Graysay
*Attorney, Agent, or Firm*—M. Reid Russell

[57] ABSTRACT

A bone fixation and fusion system, that is preferably for use for joining bone ends together, and includes two members, that are each for individual turning into bone material, and include, respectively, male and female connector ends, that are for fitting together to connect together the member ends, bringing the bone material wherein they are turned into engagement and once connected resist being pulled apart. The connector ends are, respectively a cylindrical sleeve that extends axially from one member rear face, that includes a ring formed around the cylinder end and is cross cut longitudinally from that ring end, to form a spring collet, with the other connector end consisting of a cylindrical cavity that is formed longitudinally into the other member rear face for receiving the spring collet therein, which cylindrical cavity may include a groove, grooves or threads formed in the cavity wall that the spring collet ring end flexes into to provide a resistance to the two members being pulled apart. Each member includes a tool engaging end for receiving a turning tool fitted thereto, with threads formed around the member body, and provides, in the embodiment a twist drill as a member forward end for turning into the bone material. The system can be configured for use in a dental procedure where a ceramic or plastic crown or bridge can be formed on one member for installation onto the other member that has been turned into a patient's jaw, or one of the members can be configured as a bone joint fusion member.

16 Claims, 6 Drawing Sheets

BONE FIXATION AND FUSION SYSTEM

BACKGROUND OF THE INVENTION

1. Field of the Invention

This invention relates generally to orthopedic devices for installation in surgical procedures to position and maintain in opposing ends of a bone together during healing.

2. Prior Art

Maintaining together bone ends of cancellous/cortical bones during a bone knitting or healing process has, in the past, presented a myriad of problems to a treating podiatrist or orthopedist. Particularly, where the bone repair is undertaken on a small bone, such as a broken finger or toe bone that, such have involved a procedure that includes drilling with a K wire, or the like, from a joint through the broken ends, and through the finger or toe end. Which K wire remains in place during bone healing, and is then removed in a second procedure. Like such K wire technique, fixation pins, have been utilized in a fixation of mallet fingers, shaft fracture, and epiphyseal separation, and are installed through the digit end to pass through the joint or fracture.

Where a use of fixation pins and devices for drawing broken bone sections of large bones are common, and examples of such are shown in patents to Lundholm, U.S. Pat. Nos. 2,570,465; to Cochran, et al, 3,103,926; and to Freedland, 4,409,974, with small diameter bones, such arrangements are not practical. Also, for bone fixation, additional to the K wire and fixation pins discussed above, a number of draw pins, bars and staples have been developed. Some examples of draw pin and splint arrangements are shown in patents to Reese, U.S. Pat. Nos. 4,688,561 and to Cox, 3,744,488. Draw bar apparatus for mounting to the bone side to pull broken bone ends together, are shown in patents to Sutter, et al, U.S. Pat. Nos. 4,388,921; to Wu, 4,570,624; and to McKinney, 5,167,665. Additionally, staple devices, including an adjustable staple, are shown in patents to Medico, U.S. Pat. Nos. 4,913,144 and to Gilmer, Jr., 4,723,540; and a variety of staple devices are shown in patents to Shapiro, U.S. Pat. Nos. 4,414,967; to Borzone, 4,278,091; to Pratt, et al, 4,438,769; to Crainich, 4,607,638; to Gauthier, 4,838,254; and to Sheehan, 5,053,038. None of which devices, however, is like the present invention that provides individual couplings that are for mounting, respectively, in the bone opposing faces to align with one another and snap together. Which device tightly couple and maintain the bone ends together during the bone healing or knitting process.

The above cited patents illustrate earlier devices that employ structures and procedures either for fitting a pin, or the like, from a joint to a bone end for pulling bone pieces together; provide for fitting a pin device across broken bone ends; or provide for installing a staple or draw bar arrangement, or combination thereof, onto a bone exterior to pull broken bone opposing end faces together. Such earlier devices and procedures as involve longitudinal or lateral pinning are highly invasive, and staple and draw bar devices are often impractical for use with small bones. The present invention, unique therefrom, provides a procedure that is minimally invasive in that it provides for turning coupling members into opposing faces of a broken bone that are arranged to snap together for both maintaining bone end faces in alignment and to maintain a minimum contact pressure therebetween so as to promote the bone ends or sections knitting or healing together. The individual couplings members preferably each include a section of threads formed therealong for turning into the bone material and individually include male and female coupling ends that extend, respectively, from the bone opposing end faces for joining together.

To provide for turning into bone ends, the members either are for turning into pre-drilled holes or each employs a trust drill that extends axially from a forward member end with a threaded mid-section, and with a male or female coupling extending axially from a rear end. Which drill end and threaded mid-section are similar to an anchor device shown in a prior patent of one of the inventors identified as, a "Suture Anchor Assembly", U.S. Pat. No. 4,632,100, which device is shown utilized in later U.S. Pat. Nos. 4,927,421 and 5,037,426. The devices, of these patents, however, show arrangements for anchoring a suture, or the like, onto a bone surface, and are shown for use as an interference screw, rather than a bone fixation system that includes interactive coupling ends for joining and maintaining bone ends faces and systems together in proper alignment so as to a minimum resistive force to separation of which bone surfaces.

SUMMARY OF THE INVENTION

It is therefore, a principal object of the present invention in a bone fixation system to provide a system for coupling bone ends together.

Another object of the present invention is to provide, a pair of interactive members as the bone fixation system, each for implanting in an opposing bone end face, such that a coupling end of the one member, that extends axially therefrom, will fit into a cylindrical cavity formed longitudinally in the other member that couple together to draw and maintain the bone end faces together.

Another object of the present invention is to provide, as the male coupling member, a cylindrical sleeve that projects from a threaded body portion of the member that includes a ring formed around its opposite end, and provides for longitudinally cross-cutting ring end, to a mid-section of the cylindrical sleeve forming a spring collet that is to fit into a longitudinal cylindrical cavity formed in the other members threaded body portion for maintaining the spring collect therein.

Another object of the present invention is to provide an arrangement where the member cylindrical sleeve will travel to and be maintained at a selected depth in the other member cylindrical cavity to provide a coupling that will exhibit a sufficient resistance to being pulled apart for connecting and maintaining the bone end faces together to promote proper healing.

Still another object of the present invention is to include, with the threaded body portions of each member, a fluted drill that is mounted axially from a forward end thereof, and is for turning into a bone end to where the body portion threads engage and themselves turn into the bone material to a desired depth.

Still another object of the present invention is to provide a sided section on the body portion that is adjacent to a member rear end for receiving a tool end there over for turning the member into the material of a bone end face.

Still another object of the present invention is to provide a versatile coupling system that can be used for; joining broken bone ends together, so as to maintain the bone end sections together; for use in surgical procedure to fuse a joint; and is even useful for mounting of appliances to bone, such as a crown or bridge in a patients's mount in a dental procedure.

Still another object of the present invention is to provide a bone fixation system and procedure for its use that is simple to use and as minimally invasive for the repair of small bones, as found in a persons hand or foot, can further be utilized in operations for involving a fusing of a patients joint, and is even useful in dental procedures for providing anchors for mounting a crown or bridge in a patient's mouth.

In accordance with the above set out objects, the invention is in a bone fixation system that includes a pair of members, that are each for turning into a bone face. The members include a male coupling portion that is preferably a cylindrical sleeve that extends from a rear end of one member with a female cavity formed in the other member end that is for receiving the male coupling end. Additional to their coupling ends, each member includes a cylindrical body that is externally threaded, and may include a twist drill extending axially from the cylindrical body forward end that is opposite to the coupling end. Or, alternatively, the external threads may be sloped from the threaded cylindrical body to terminate in a pointed forward end, for turning into a pre-drill hole formed into the bone material.

For turning each member, turning the fluted drill into the bone material to where the threads engage and turn into that bone material, a sided collar or section is formed around the member body. This collar or section is preferably arranged between the threaded portion and the connector end, and is for receiving a driver, that has a cavity with a like sided interior wall, fitted there over, the turning of the driver to turn the member also.

The male member coupling end, consists of the cylindrical sleeve that extends axially from the member rear end and includes a ring collar formed around a top or outer end thereof. The ring collar and sleeve are cross cut longitudinally to a mid-section of the sleeve to provide for an inner flexure of the ring collar and sleeve segments when a compressive force is exerted thereagainst, functioning as a spring collect. The female member of the pair of members includes, in a rear end, the cylindrical axial cavity that is of a diameter to somewhat resist passage of the male member ring collar end of the sleeve fitted thereon so as to provide a compressive force that flexes the ring collar and sleeve segments inwardly to allow such passage.

The female member cylindrical cavity can include a single continuous groove, or a number of spaced apart continuous grooves, formed around the cavity wall at a desired depth or depths therein from the member rear end. The continuous groove or groves are each to receive the sleeve ring collar end that can flex outwardly into each groove, for resisting the members being pulled apart. The continuous grooves allow for setting the member coupling relative positions and provide a resistance to the members being pulled apart. Alternatively, a number of fine pitch threads, shallow grooves, or the like, can be formed around the cavity wall to provide for infinite positioning of the sleeve ring collar in which cavity, while still providing for a desired pull apart resistance.

The male and female members are for turning, respectively, into opposing faces of bone ends, the member coupling ends to align and fit together when the bone ends are fitted together in proper registry. Additionally, the male and female members of the invention can be used to repair of a broken bone, for the fusing of a joint, and further, the members of the invention can be configured for use for mounting a dental prosthesis. For such dental use, one of the members is preferably arranged for turning into and permanently seating in a persons jaw bone, with the other member to function as a metal coping whereon a crown or a section of a bridge is fabricated, the coping for fitting onto and locking to the member that is seated in the bone.

In practice, in a surgical procedure for maintaining broken bone ends together during healing, such as a bone as is found in a patient's hand or foot, the patient's skin at the broken bone ends is opened and the broken bone ends are pivoted apart. Opposing points on the broken bone surface are located that will align when the broken bone faces are properly together are determined. This determination can be made by turning one of the bone fixation and fusion system members into one broken bone end, aligning the bone faces, and urging the other broken bone end thereagainst to mark the aligning point on which other broken bone end face.

Each of the members preferably includes a fluted drill extending axially from a forward face that is turned into the broken bone face. Alternatively, in another embodiment of the invention, opposing points on the broken bone end faces can be drill and pointed threaded members of the invention can then be turned therein. The members are individually turned into the broken bone end faces so as to seat each member to a depth therein where, when the member coupling end are telescoped together, the members will be locked together and, the broken bone end faces pulled together into close fitting engagement. A similar seating procedure is employed where the invention is arranged for use in a dental procedure that involves mounting a crown or bridge that has been built up on one of the members onto the other members that has been seated in a patient's jaw bone. Which procedure may further include application of an adhesive for permanently coupling the members together.

The foregoing and other objects, features and advantages will become more fully apparent from the following description of the preferred embodiments of the invention as illustrated in the accompanying drawings.

THE DRAWINGS

Figure 1:
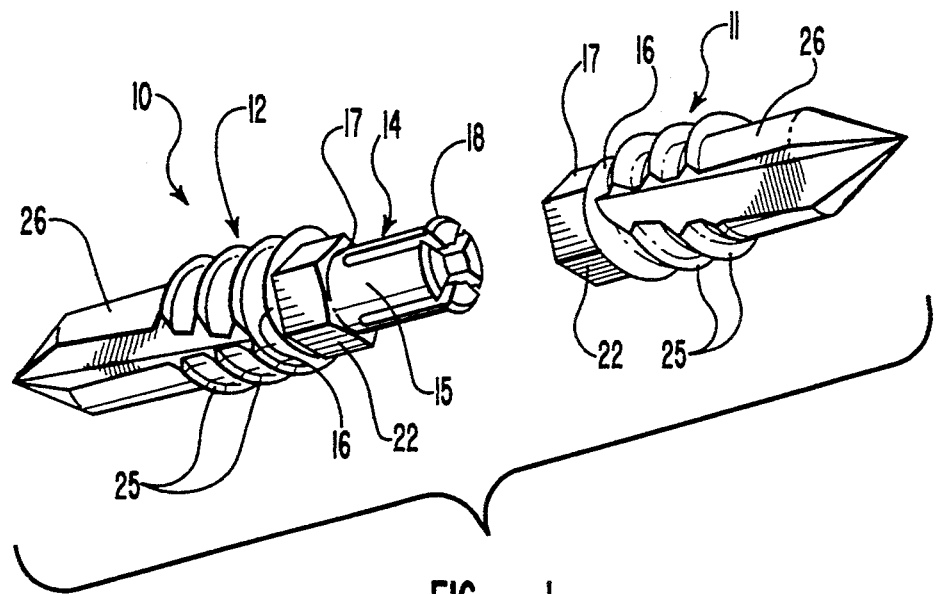
FIG. 1 is a profile perspective view of one embodiment of a pair of members of a bone fixation and fusion system of the invention shown exploded apart, a male cylindrical sleeve coupling axial end of one member shown aligned for fitting into a female longitudinal cylindrical cavity of the other member.
Figure 2:
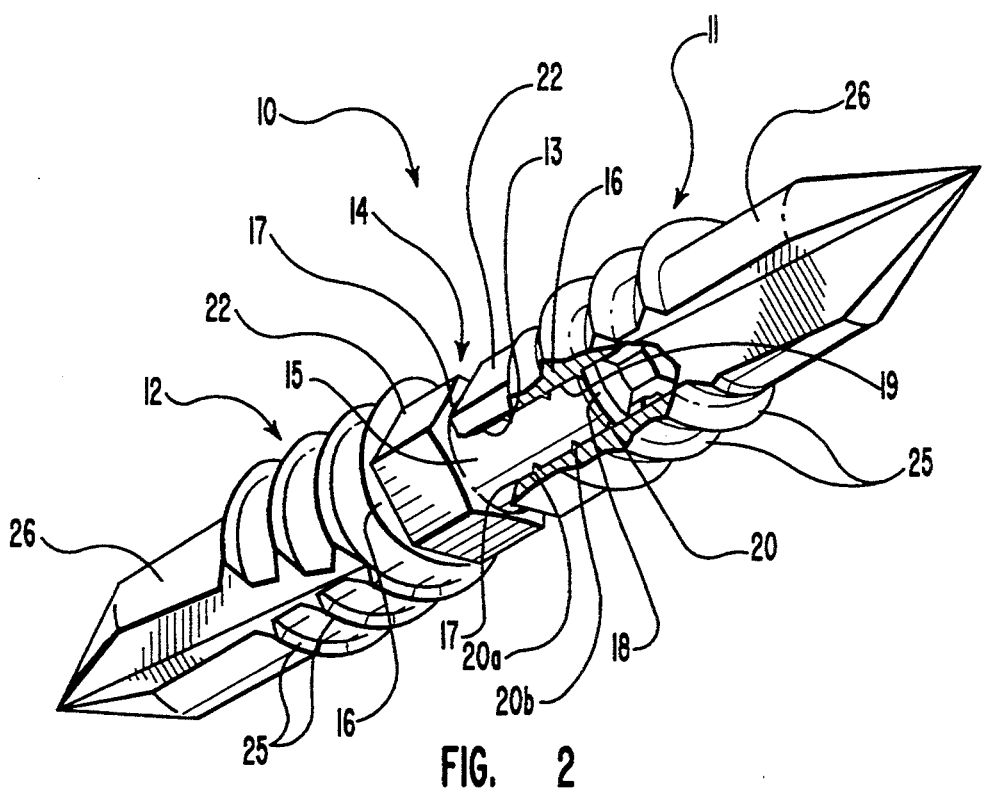
FIG. 2 is an view of the profile perspective view of the pair of members of FIG. 1 shown fitted together.
Figure 7:
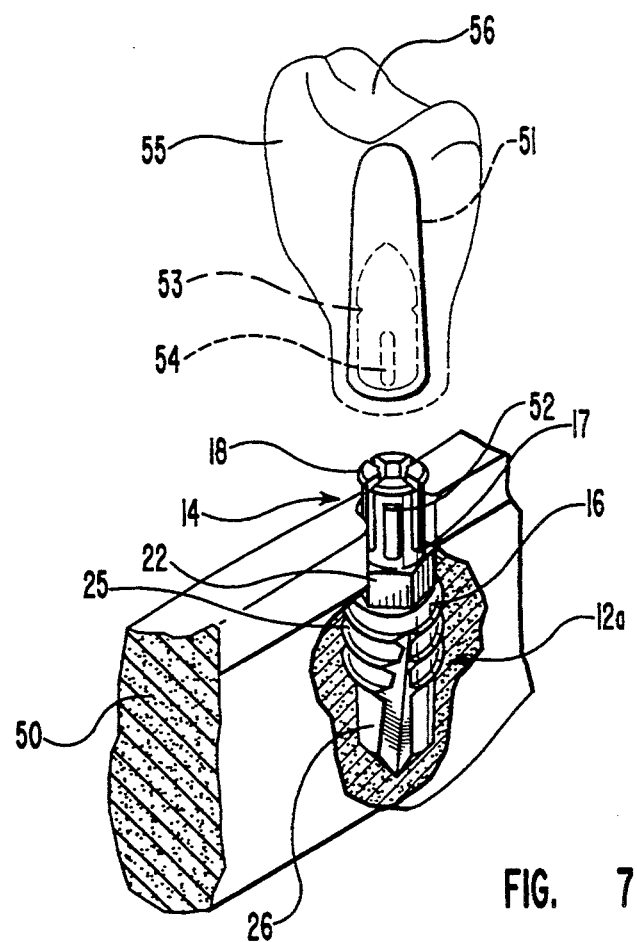
Figure 8:
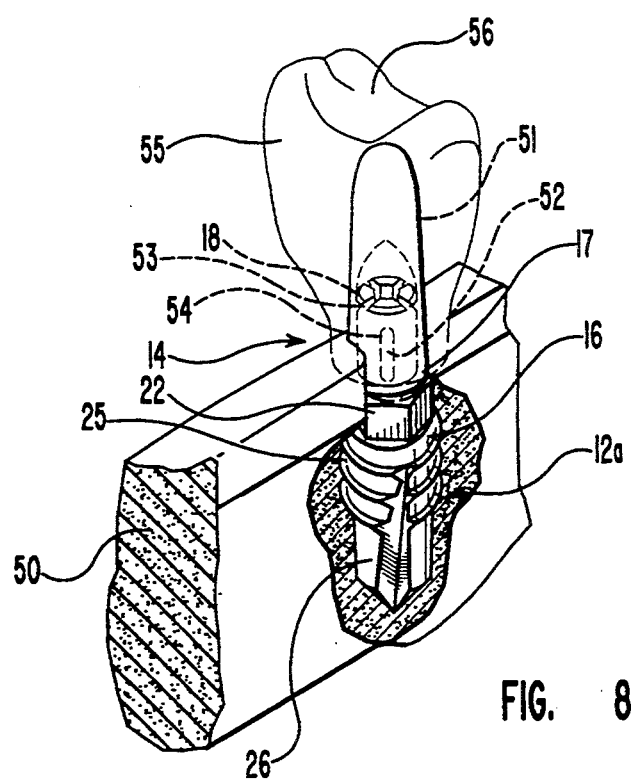
Figure 9:
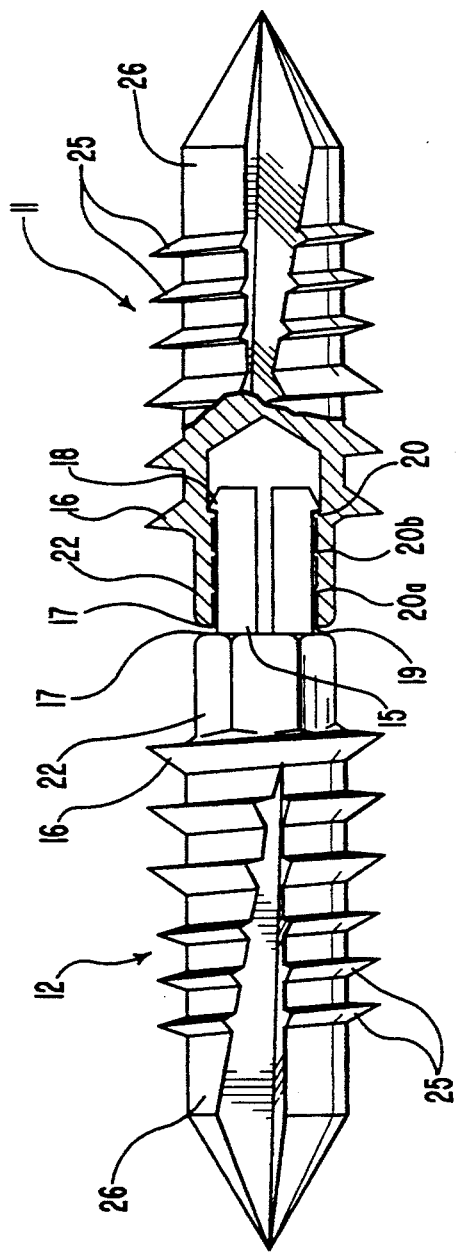
Figure 10:
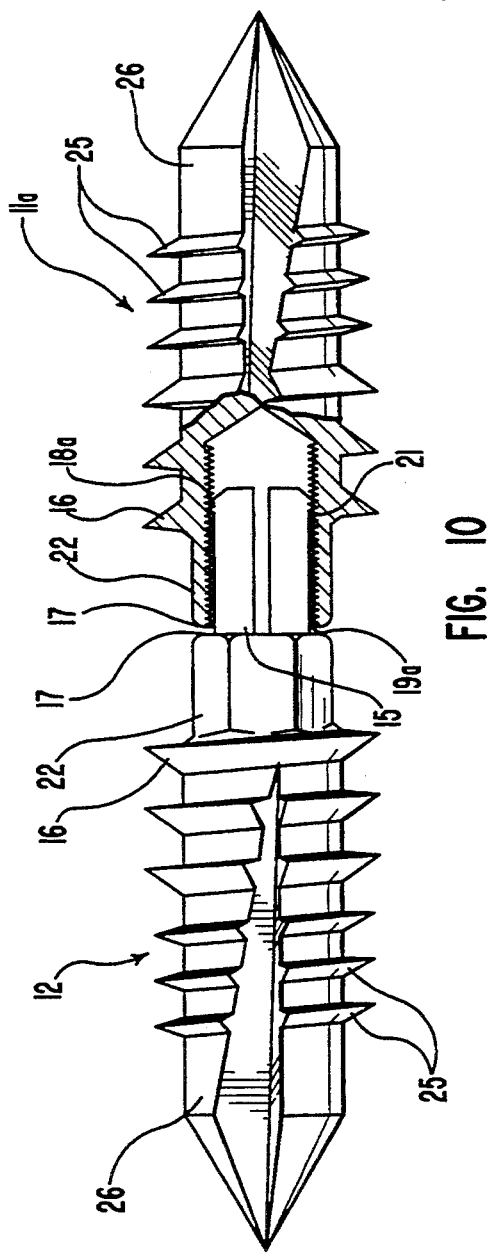
Figure 11:
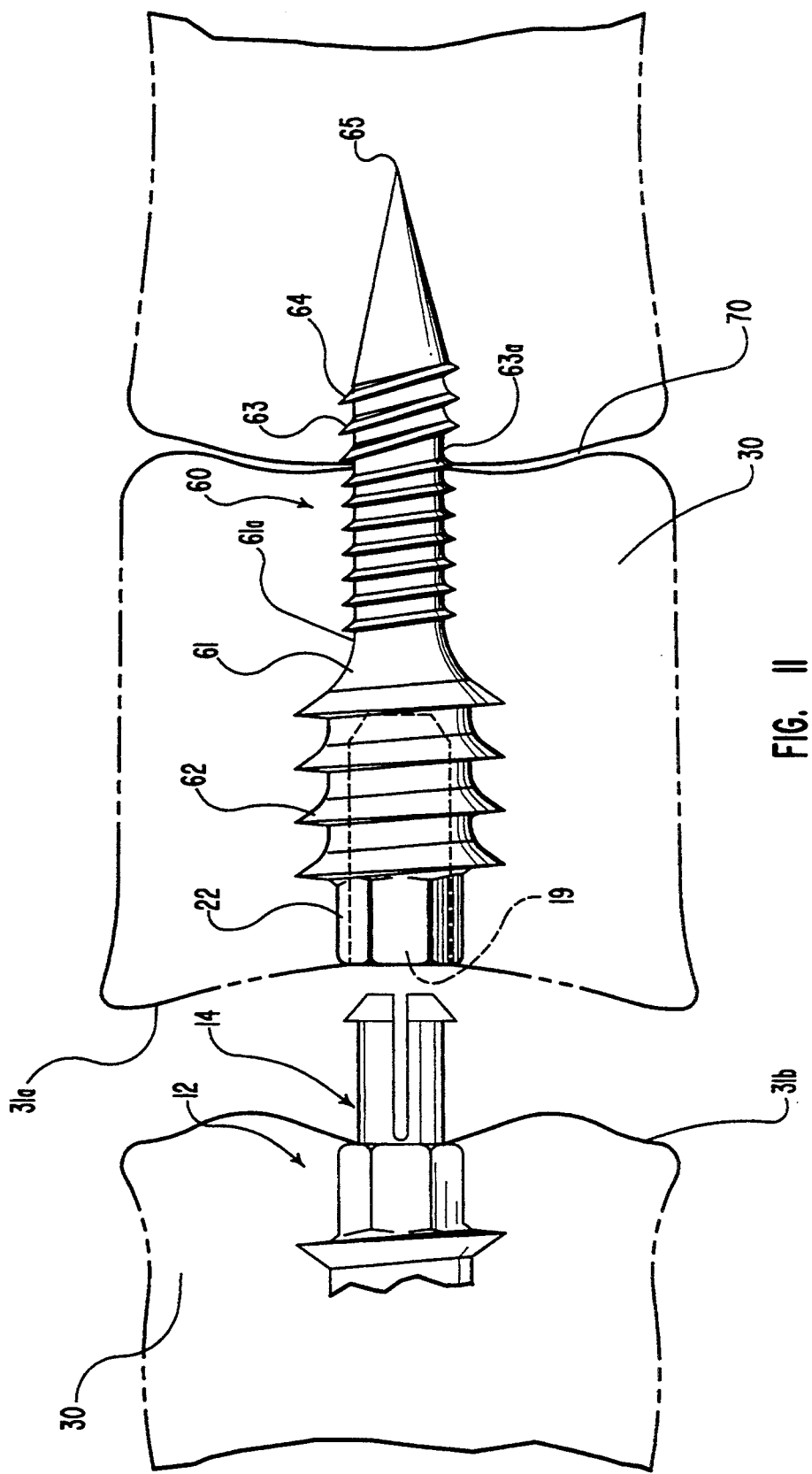

FIG. 7 is a profile perspective view of a section of a patient's jaw bone showing a male connection member turned into the jaw bone such that the coupling end extends at approximately a right angle upwardly therefrom, and showing a female member formed as a smooth coping whereon a reproduction of a tooth is shown formed, the female member shown aligned for fitting onto the male member coupling end;

FIG. 8 is a view like FIG. 7 only showing the female member, whereon the tooth reproduction is formed shown seated on the male member coupling end;

FIG. 9 is a side elevation view like that of FIG. 2 showing the pair of members connected together, with an end section of the female member shown broken away to expose the cylindrical cavity therein that is shown to include a forward groove where the ring end of the male coupling member is shown seated providing a collect and barrel interface, and showing, spaced grooves formed in the cavity at intervals therealong as alternative male member ring end positioning sites;

FIG. 10 is a view like that of FIG. 9 showing another embodiment of the female member where the member cylindrical cavity is threaded therealong, with the ring end of the male coupling member shown resting between thread flights, providing a collet and barrel interface; and FIG. 11 is a side elevation of still another arrangement of a bone fixation and fusion system showing a male member that is like that of FIGS. 1, 2, and 6 through 10, turned into a bone end face and is arranged for coupling to a female member that is shown as having a body with a pointed end opposite to its cylindrical cavity end and includes a pair of spaced apart threaded sections formed there around, the female member is shown turned through a bone face and through an adjacent joint for both joining the bone end faces together and for providing a fusing of the adjacent joint.

DETAILED DESCRIPTION

The invention is in a bone fixation and fusion system that includes a pair of members that are for individual turning longitudinally into opposing bone ends. The members including, respectively, male and female coupling ends, that are to be fitted together to maintain the bone end faces couples closely together during bone healing. The coupling preferably exhibits a minimum resistance to being pulled apart that, in practice, is approximately three(3) pounds, but can be greater or lesser within the scope of this disclosure. As set out below, the invention can be utilized for maintaining a variety of sizes of human bone ends together, including but not limited to broken bone ends, during healing, but is preferably utilized on small bones like those found in a patient's hand or foot, and, in one embodiment, can also provide for fusing a patient's joint.

A first embodiment of the invention in a bone fixation and fusion system 10, hereinafter referred to as system 10, is shown best in FIGS. 1, 2, 5 and 6, as consisting of a pair of members 11 and 12. The members 11 and 12, as shown best in FIGS. 2 and 6, include, respectively, a female connector 13 and a male connector 14, that are for interconnection to join and maintain opposing end faces 31a and 31b of a bone 30 together shown as a broken bone 30 in FIGS. 3, 5 and 6. To provide this intradigital joining, the male connector 14 is formed as hollow cylindrical cylinder or sleeve 15 to extend axially from a rear face 17 of the member body 16. The hollow cylinder 15 includes a ring 18 formed around its end that is opposite to its mounting to rear face 17; the hollow cylinder 15 is longitudinally cross cut through the ring 18 to a cylinder mid-section, forming a spring collet. So arranged, the spring collect formed by the hollow cylinder 15 and ring 18 consists of sections that can be flexed towards one another when compressed, and will spring back to their original attitude when the compressive force is released. To join the members 11 and 12 together the member 11, shown as a female member, includes a center longitudinal cylindrical cavity 19 formed therein, hereinafter referred to as cavity. As shown in FIGS. 2, 9 and 10, the cavity 19 has a diameter to just accommodate and will compress the spring collet sections fitted therein.

To provide for coupling of the members 11 and 12 together the member 12 cylinder end ring 18 is fitted into the member 11 cavity 19 and is slid therein to where the ring 18 aligns with a groove 20 that has been formed around the cavity 19 wall, as shown in FIGS. 2 and 9. Thereat, the ring 18 outer edge will seat in the groove 20 as the cylinder and ring sections flex outwardly, locking the member 12 cylinder 15 in the member 11 cavity 19. In which locking the spring force of the spring collet sections at the junction of the ring 18 and groove 20 discourage rotation of the members 11 and 12 relative to one another. In practice, to separate the members 11 and 12, by pulling the cylinder 15 out of the cavity 19, requires a certain pulling force to support the members, in practice a pulling force of approximately three (3) pounds is applied to separate the members. Though, it should be understood the components could be arranged to require an application of a greater or less pull-apart force to separate them within the scope of this disclosure. Such applied force pulls the ring 18 against the groove 20 side to recompress the spring collet sections together thereby allowing the cylinder to be pulled out from the cavity 19. A requirement for a minimum pull-apart force is to provide for a maintenance together of bone end faces during the healing process.

To provide for a number depth settings for travel of the member 12 cylinder 15 into the member 11 cavity 19, a plurality of spaced grooves 20a and 20b, that are additional to groove 20, are shown in FIGS. 2 and 9, as having been formed at intervals along and around the cavity 19 wall. The cylinder 15 of member 12 is thereby positionable at succeedingly greater distances into the member 11 cavity 19 to provide for coupling adjustability so as to compensate for the difference from an optimum depth of seating of member 11 or 12 into the bone. Additionally, FIG. 10 shows another member 11a that is for use with member 12 for the bone fixation and fusion system, that provides for an infinitely variable seating capability to member 12 cylinder 15 along a cylindrical cavity 19a of member 11. Shown therein, the cavity 19a is threaded, or includes a plurality of closely spaced grooves, identified as threads 21. Ring 18 is shown resting between two threads 21a which seating also provides a required resistance to the separation of members 11a and 12.

In practice, the described members, 11, 11a and 12 can be pulled apart when a sufficient force is exerted to separate the members. When such separating force is applied, the cylinder and ring sections are flexed inwardly as the ring 18 is pulled out of groove 20 or across threads 21. Also, it should be understood, that the cylinder 15 may be formed of a sufficiently stiff material and have a diameter that, when longitudinally cross cut, will provide a spring collet, that has a sufficient resistance to flexure that the cylinder end ring 18 surface that engages the cavity 19 wall alone will exhibit a sufficient resistance to movement to provide a required resistance to being pulled apart, thereby eliminating a need for grooves 20, 20a, pr 20b, or threads 21 to be formed in the cavity 19 or cavity 19a walls.

Hereinabove has been set out preferred coupling arrangements for joining members 11 and 12. Except for the member female and male connectors 13 and 14, respectively, the members 11 and 12, in the embodiments of FIGS. 1 through 3, 5, 6, 9 and 10 are essentially alike. Shown therein, each member 11 and 12 includes a cylindrical body 16 with the cylinder 15 extending axially from an end face 17 thereof, or has the cavity 19 formed longitudinally through end face 17 and into the body 16. Each member 11 or 12 also includes a sided tool engaging section 22, that is formed around the body 16, adjacent to the end face 17, and has a hexagonal cross section. Illustrated in FIGS. 3 and 5, the sided section 22 of both members 11 and 12 is for receiving a turning tool 23 end 24 that is fitted there over. Which turning tool end 24 is shown as having a longitudinal cavity formed therein whose interior wall is sided, like that of the sided tool engaging section 22, and is for making contact therewith to transfer tool 23 turning into member 11 or 12.

Figure 3:
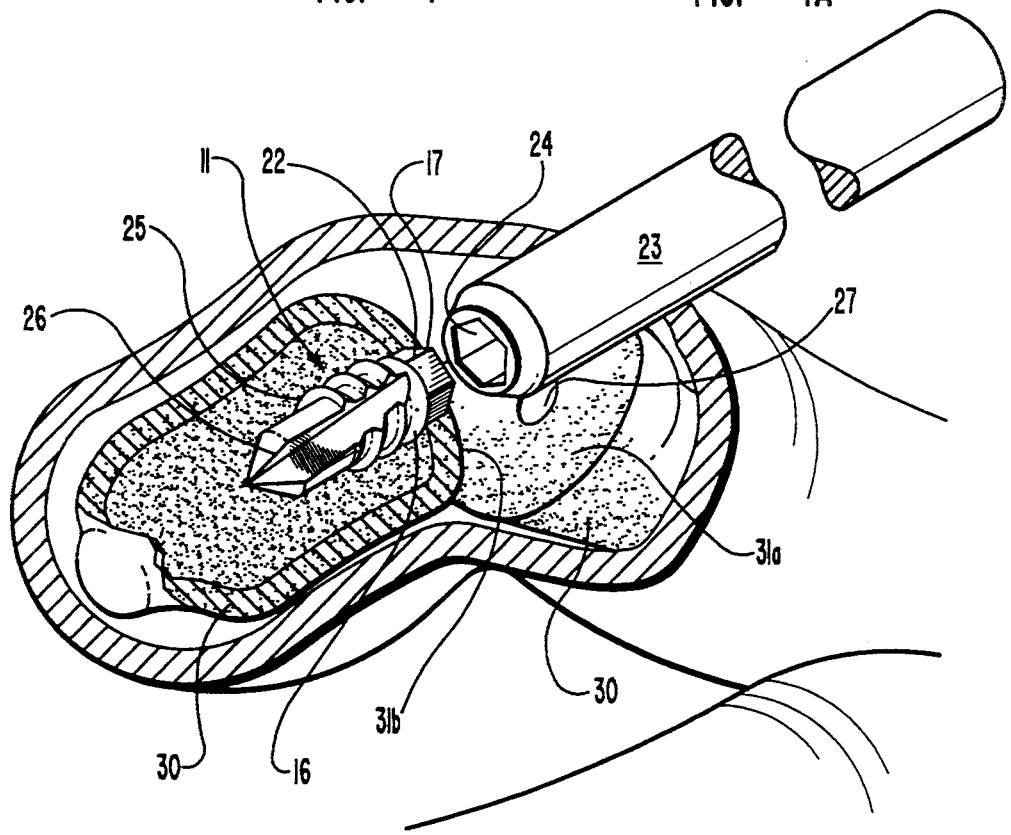
FIG. 3 is a profile sectional view of an end portion of a patient's broken finger, showing a female member of the pair of members of FIGS. 1 and 2 being turned longitudinally by a tool into a proximal bone surface at the break.
Figure 5:
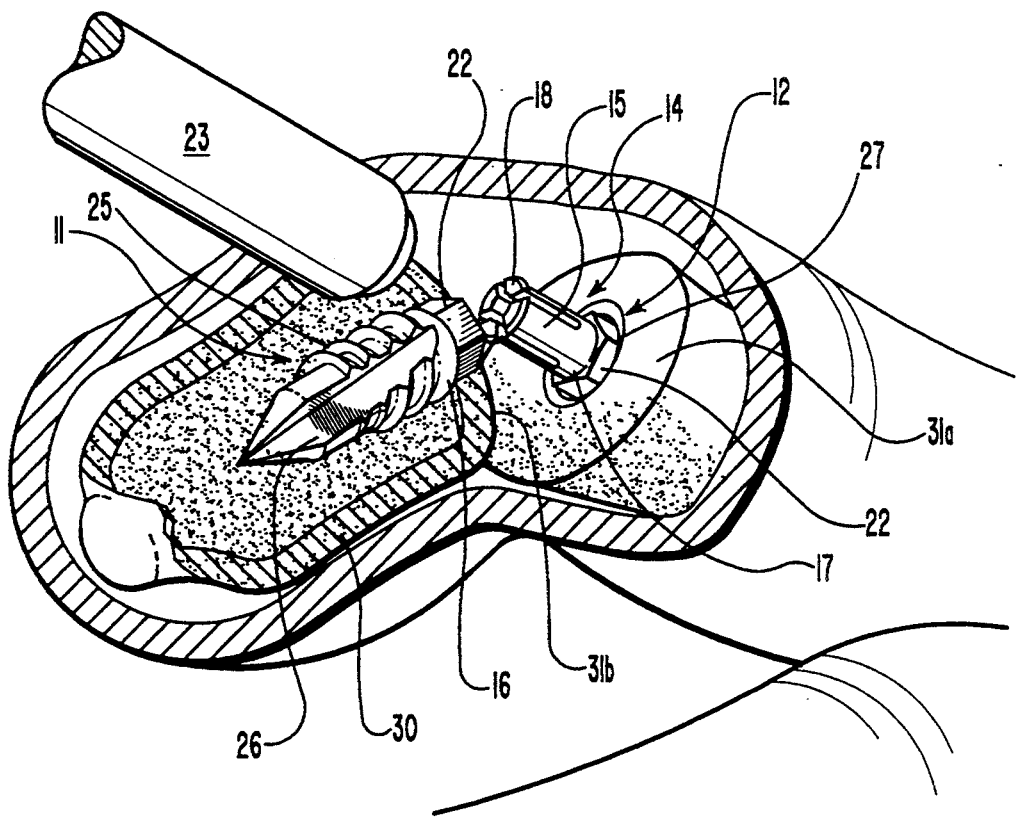
FIG. 5 is a view like that of FIG. 3 only showing the male member of the bone fixation and fusion system of FIGS. 1 and 2, as having been turned by a tool into the distal bone surface at the break.
Figure 6:
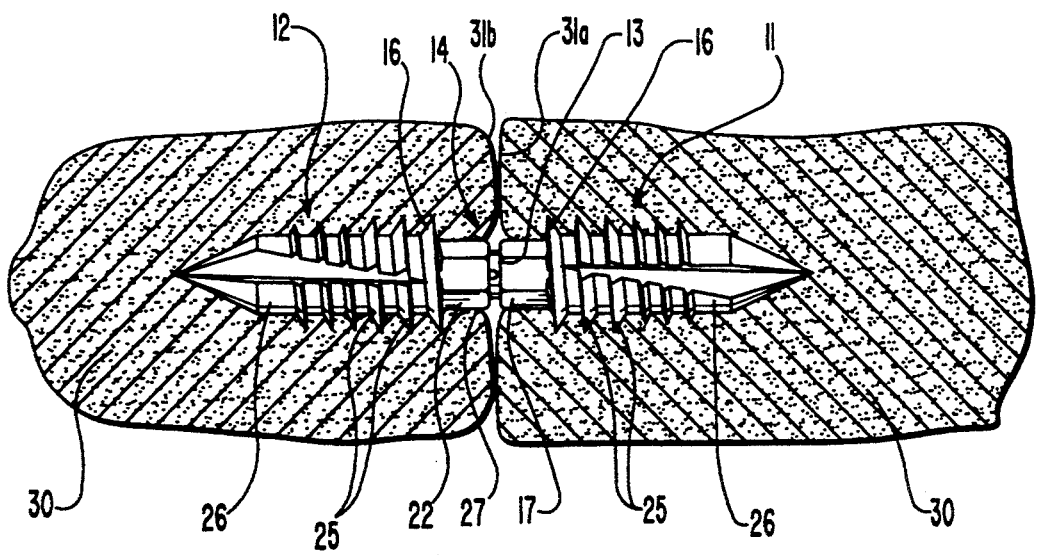
FIG. 6 is a side elevation longitudinal sectional view of the broken bone of FIGS. 3, 4 and 5, showing the male connection member fitted into the female connection of the bone fixation and fusion system, with the broken bone end faces shown maintained tightly together.

Each member 11 and 12 is, as set out above, for turning utilizing tool 23, into a face 31a or 31b of an end of a bone 30. FIGS. 3, 5 and 6 show the members 11 and 12 fully seated in each bone end and coupled together. For turning into bone 30, each member 11 and 12 includes a plurality of threads 25 that are formed around a mid-section of cylindrical body 16. To penetrate the bone face, a twist drill 26 is shown secured to the body 16 forward to extend axially as a forward extension of the body.

For example, at a break in bone 30, that is preferably small bone, such as one found in a patient's hand or foot bone, as shown in FIGS. 3 through 6, the bone is broken into opposing distal and proximal faces 31a and 31b, respectively. Shown in FIG. 3, with the patient's skin opened at the break, the tool 23 turning end 24 is fitted onto the member 11, the turning end 24 opposing sided sections to engage for turning to seat the member longitudinally through the face 31b into approximately the bone 30 center, as shown also in FIG. 6. Thereafter, a point 27 in the broken bone face 31a that is immediately opposite to the center of the member 11 cavity 19 is determined. The male member 12, as illustrated in FIG. 5, is then turn into which point 27 on the broken bone face 31a. Thereafter, the member 12 cylinder 15 is fitted into the member 11 cavity 19, as illustrated in FIG. 6, and urged therein to where the opposing broken bone end faces 31a and 31b of bone 30 are positioned in close engagement with one another.

In the embodiment of FIGS. 1 through 3, 5, 6, 9 and 10, six threads are shown formed along the body 16 from adjacent to the side section 22 to the fluted drill end 26. The threads are shown as being deep threads. The threads each form essentially a right angle to the body. Deep threads are formed to provide a large surface engaging area that is accordingly resistive of being pulled out to the bone material at a bone center.

Figures 4, 4A:
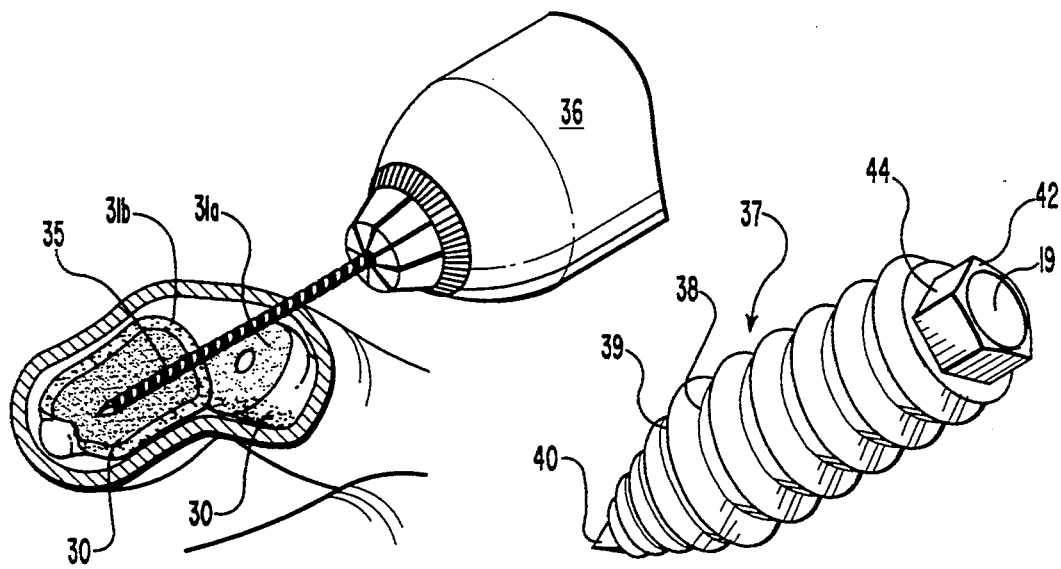
FIG. 4 is a reduced view of the end portion of the patient's broken finger of FIG. 3, showing a drill being turned longitudinally therein.
FIG. 4A is a profile perspective view of another embodiment of a female member of a bone fixation and fusion system, that is for turning longitudinally into the hole drilled into the broken bone end utilizing a drill, shown in FIG. 4, the female member for turning in the drilled hole utilizing a tool like that shown in FIG. 3.

Alternative to the combination of fluted drill 26, set out above, for turning into a bone center to where the first of threads 25 turns into the bone material, FIG. 4, shows the bone 30 broken apart with opposing bone faces 31a and 31b and center holes being drilled into the bone faces. Utilizing a drill that is turned by an electric drill 36. Which drill travels a short distance longitudinally into the bone center and is to provide a hole 35 for receiving a member 37, shown in FIG. 4A, turned therein. The member 37 can be either a male or female member, depending upon the gender of the connector end secured thereto. The member 37, as shown in FIG. 4A, is a female member that, like member 11, includes cylindrical cavity 19, formed through a face 42 of a sided section 41. Which sided section 41, is like sided section 22 of members 11 and 12, and is an end of a member body 38. Threads 39 are formed around the member body 38 that are like threads 25 of members 11 and 12 except they extend the length of the body 38 from the sided section 41 and tapper inwardly to a pointed forward end 40. The pointed forward end 40 is for fitting into the hole that has been drilled into either of the bone faces 31a or 31b. The member 37 is turned therein to where a leading thread 39 engages and turns into the bone 30, with the other member threads 39 following, to where the member 37 is fully seated in the bone 30.

The members 11, 12 and 37, as discussed above, are each for use in joining and maintaining bone ends together during bone healing. Additionally, as illustrated in FIGS. 7 and 8, the invention can be adapted for use in a dental procedure for replacing a patient's missing tooth or teeth with a crown or bridge. Further, as shown in FIG. 11, the invention can include an elongated member 11 or 12 one of which may include with two sets of spaced threads with the member for both fitting and maintaining bone ends together and is additionally for fusing a joint that is adjacent to such bone ends. Which embodiments are shown in FIGS. 7, 8, and 11, and are set out and further discussed hereinbelow.

FIGS. 7 and 8 illustrate another embodiment of the invention that is for use in the manufacture and installation of a replacement crown or bridge in a dental patient's mouth. For this use, one of the members 11 or 12, shown in FIGS. 7 and 8 as anchor member 12a, that includes a male connection member 14 and is turned into a patient's jaw bone 50, seating therein as an implant. In which seating, the member 12a is turned well into the patient's jaw bone, and the male connection member 14 is of an appropriate length to extend out through the patient's gum for receiving, a female member 51 fitted thereon. The female member 51, as shown, has a tooth representation 55 formed thereon with anatomy on the crown surface 56 to interact with the anatomy of an opposing tooth. To provide for a proper registry of the female member 51, tooth anatomy with an opposing tooth exact positioning on member 12a must be provided. To provide which positioning and registry, a longitudinal ridge 52 is preferably formed along the outer surface of cylinder 15 that extends the length thereof. The ridge 52 is to slide along a groove 54 as a spline, shown in broken lines, that is formed longitudinally in the wall of a cylindrical cavity 53 that is formed in female member 51. The female member 51, as set out maintains a tooth 55 built up thereon. Which buildup is provided by covering the member 51 smooth outer surface with porcelain for firing and shaping, or, as determined, covering it with a plastic for light curing, or the like, for forming the tooth representation or crown 55 thereon. To facilitate this manufacture the member 51, has a smooth outer surface rather that the threads, or threads and fluted drill, of the other members 11 and 12.

As set out, the crown 55 includes a tooth anatomy 56 formed in its top surface that must be in registry with the anatomy of an opposing tooth or crown. The arrangement of the longitudinal ridge 52 of cylinder 15 for traveling along the groove 54 of the female member 51 provides for this required the registry. This registry of the female member 51 to the member 21a allows a dental technician to build up the crown on the female member where the anatomy 56 will be in proper meshing engagement with the anatomy of an opposing tooth or crown. For seating which female member 51 onto the member 12a the cavity 53 can include the single groove or plurality of grooves formed there around, as shown in FIG. 9, or can include the threads or shallow grooves, as shown in FIG. 10. Or, for permanent seating of the female member 51 onto member 12a, a dental adhesive can be applied therebetween.

Additional to the dental embodiment of the invention, as set out above, in FIG. 11 is shown a fusion member 60, that can be a male or female member, and is shown in FIG. 11 as a female member. Fusion member 60 includes a cylindrical body 61 with a sided section 22 formed in one end wherein a cylindrical cavity 19, shown in broken lines, is formed. The cavity 19 is to receive the male connector 14 end of member 12 fitted therein, functioning as described above with respect to a description of the connection of members 11 and 12. The fusion member 60 includes threads 62, that are preferably like the threads 25 of members 11 and 12, formed around the body 61, immediately forward of sided section 22. Threads 62 are like the threads 25 and are for seating in the bone 30 as illustrated in broken lines. Ahead of threads 62, the body 61 tapers inwardly at 61a to a lesser diameter section that includes threads 63 formed therearound. The threads 63 are preferably shallower than threads 62, and change in pitch at 63a to threads 64 that have a same thread height but are at a greater pitch and taper inwardly to a forward body section that terminates in a pointed end 65. In practice, as illustrated in FIG. 11, at a break in bone 30 a hole is drilled into face 31a that extends across a joint 70, which hole drilling is followed by turning of the fusion member 60 pointed end 65 through the hole to travel across joint 70, providing a joint fusion. After which turning the cylindrical cavity 19 that is formed in the fusion member sided section 22 is positioned beneath the broken bone end face 31a to receive a male connector 14 end of member 12. Anticipating this connection, the member 12 will have been turned into the opposite broken bone end face 31b. Coupling the member 12 and fusion member 60 together maintains the bone 30 faces 31a and 31b together, as illustrated in FIG. 6, and also provides for fusing joint 70 that is adjacent to the bone faces.

As set out above, while the members of the bone fixation and fusion system of the invention can be sized for used in joining large bones, they are preferably sized for use in procedures involving repair of small bones. For example, the bones of the hand, and foot. Accordingly, for such use, the members will have a very small diameter, with the length of member 60 determined by the distance from bone faces 31a and 31b to a joint that is to be fused. For which uses, as set out above, the connected members male collet and female barrel configurations are to provide at least a minimum resistance to being pulled apart. Also, as the members are for human implantation, each shall be manufactured from a material, such as titanium, stainless steel or other metallic materials, that is suitable for human implantation. For some applications, as for example when the faces 31a and 31b of bone 30 are drilled to receive a threaded member turned therein, such as members 37 and 60 therein, a biodegradable material be utilized to construct the members, that will later be adsorbed during the healing process, within the scope of this disclosure.

While preferred embodiments of our invention in a bone fixation and fusion system have been shown and described herein, it should be apparent that this disclosure is made by way of example only and that variations are possible within the scope of this disclosure without departing from the subject matter coming within the scope of the following claims, and a reasonable equivalency thereof, which claims we regard as our invention.

We claim:

1. A bone fixation and fusion system comprising:
    a pair of members each including a cylindrical body having a rear face,
    a male connector means and a female connector means for coupling the pair of members;
        one of said pair of members having said male connector means and the other of said pair of members having said female connector means;
        said male connector means includes a cylindrical sleeve that extends axially from the rear face of said one member, a ring formed around a distal end of the cylindrical sleeve, and said cylindrical sleeve is cross cut from said distal ring end to a mid-section of said cylindrical sleeve, thereby forming a spring collet;
        said female connector includes a cylindrical cavity formed axially through the rear face of said other member and into said other member cylindrical body, said cylindrical cavity is formed to compress said male connector spring collet fitted therein and to release said distal ring end to return to its uncompressed attitude within said cylindrical cavity, thereby seating said male connector means therein;
    the cylindrical body of at least one of said members includes a tool engaging section;
    each of said pair of members includes means for fitting into a hole formed into an endosteum of a bone to receive and secure the respective member in said hole; and,
    each of said members includes an external surface formed thereon for connecting into said hole formed into said endosteum of said bone.

2. A bone fixation and fusion system as recited in claim 1, wherein said female connector means further includes means for resisting withdrawal of the male connector means spring collet from its seating in the female connector means cylindrical cavity.

3. A bone fixation and fusion system as recited in claim 2, wherein the means for resisting withdrawal includes at least one continuous groove formed in a wall around the cylindrical cavity to accommodate the male connector means distal ring end.

4. A bone fixation and fusion system as recited in claim 3, wherein a plurality of continuous grooves are formed in the female connector means cylindrical cavity wall at spaced intervals therealong.

5. A bone fixation and fusion system as recited in claim 2, wherein the means for resisting withdrawal includes a thread in a wall around the cylindrical cavity from end to end thereof, the space between thread flights for accommodating the male connector means distal ring end.

6. A bone fixation and fusion system as recited in claim 2, wherein both of the members include said tool engaging section;
each of said tool engaging sections comprises a sided section formed adjacent to the rear face of the respective member; and,
each means for fitting into a hole formed into said bone is a drill portion at a forward end of said respective member; and,
each said external surface of said members includes threads formed therearound.

7. A bone fixation and fusion system as recited in claim 6, wherein the threads of each said external surface taper inwardly into the drill portion forward end of the respective member.

8. A bone fixation and fusion system as recited in claim 6, wherein each drill portion is a fluted drill extending axially rearwardly from the forward end of the respective member.

9. A bone fixation and fusion system as recited in claim 2, wherein one of the members is formed as a joint fusion member with its cylindrical body formed to a length to extend from where it is seated in a bone surface to and through a joint that is adjacent to the bone surface;
said joint fusion member includes said tool engaging section; said tool engaging section comprises a sided tool section formed adjacent to said rear face of said joint fusion member cylindrical body, and said joint fusion member cylindrical body further includes a pair of spaced threaded sections that are each formed around said cylindrical body;
said pair of threaded sections including a forward threaded section and a rearward threaded section with a forward end of said forward threaded section terminating in a pointed end.

10. A bone fixation and fusion system a recited in claim 9, wherein,
said rearward threaded section of the joint fusion member is formed adjacent to the sided section;
the external surface of said other member cylindrical body having a threaded configuration which is the same configuration as the rearward threaded section of the joint fusion member;
said forward threaded section has a thread height that is less than the thread height of the rearward threaded section.

11. A bone fixation and fusion system as recited in claim 10, wherein the joint fusion member cylindrical body taper inwardly between the rearward and forward threaded sections to a lesser diameter cylindrical body forward portion that, in turn tapers inwardly from a forward portion of said forward threaded section into the pointed end.

12. A body fixation and fusion system as recited in claim 11, wherein the threads of the forward threaded section are formed with a change in pitch from approximately midway therealong towards the pointed end.

13. A bone fixation and fusion system as recited in claim 1, in combination with a means for turning said at least one member, said means for turning is a cylindrical rod that has a sided portion formed axially into one open end thereof and is arranged to engage said tool engaging section of said at least one member.

14. A bone fixation and fusion system as recited in claim 1, wherein at least one of the members is formed from a human body compatible material.

15. A bone fixation and fusion system as recited in claim 1, wherein said human body compatible material is titanium.

16. A bone fixation and fusion system as recited in claim 1, wherein said human body compatible material is a metallic material.

* * * * *